(12) United States Patent
Rodzewicz et al.

(10) Patent No.: US 11,890,170 B2
(45) Date of Patent: Feb. 6, 2024

(54) MEDICAL DRESSING

(71) Applicant: Mölnlycke Health Care AB, Gothenburg (SE)

(72) Inventors: Patrick Rodzewicz, Gothenburg (SE); Linda Mårlind, Kullavik (SE); Dennis Hansson, Gunnilse (SE); Karin Glasmästar, Hisings Backa (SE); Anna Grou, Gothenburg (SE); Conny Jakobsson, Lerum (SE); Océane Lançon, Säve (SE)

(73) Assignee: Mölnlycke Health Care AB, Gothenburg (SE)

( * ) Notice: Subject to any disclaimer, the term of this patent is extended or adjusted under 35 U.S.C. 154(b) by 695 days.

(21) Appl. No.: 16/770,156

(22) PCT Filed: Dec. 13, 2018

(86) PCT No.: PCT/EP2018/084742
§ 371 (c)(1),
(2) Date: Jun. 5, 2020

(87) PCT Pub. No.: WO2019/115685
PCT Pub. Date: Jun. 20, 2019

(65) Prior Publication Data
US 2020/0297543 A1  Sep. 24, 2020

(30) Foreign Application Priority Data

Dec. 15, 2017  (EP) .................................... 17207754

(51) Int. Cl.
*A61F 13/02*  (2006.01)
*A61F 13/06*  (2006.01)
*A61F 13/00*  (2006.01)

(52) U.S. Cl.
CPC .......... *A61F 13/025* (2013.01); *A61F 13/022* (2013.01); *A61F 13/0209* (2013.01); *A61F 13/069* (2013.01); *A61F 2013/00136* (2013.01)

(58) Field of Classification Search
CPC ........ A61L 15/00; A61L 15/58; A61F 15/008; A61F 13/069; A61F 13/063;
(Continued)

(56) References Cited

U.S. PATENT DOCUMENTS

2003/0225356 A1* 12/2003 Kulichikhin .......... A61L 24/043
602/54
2005/0059918 A1  3/2005 Sigurjonsson et al.
(Continued)

FOREIGN PATENT DOCUMENTS

EP  2001424 A2  12/2008
EP  3085344 A1 * 10/2016 ......... A61F 13/0209
(Continued)

OTHER PUBLICATIONS

JP2014168573A machine translation (Year: 2014).*
(Continued)

*Primary Examiner* — Caitlin A Carreiro
(74) *Attorney, Agent, or Firm* — Ballard Spahr LLP

(57) ABSTRACT

A medical dressing for application to a surface of a human body is described. The medical dressing has a first direction (x) of extension and a second direction (y) of extension being perpendicular to the first direction (x) of extension. The medical dressing has at least a first and a second anisotropic layer having anisotropic stiffness, wherein the stiffness of each one of the first and the second anisotropic layer is higher in the second direction (y) of extension than in the first direction (x) of extension.

16 Claims, 12 Drawing Sheets

(58) Field of Classification Search
CPC .. A61F 2013/00136; A61F 2013/00089; A61F 2013/00361; A61F 2013/00246; A61F 2013/00251; A61F 2013/00255; A61F 2013/00259; A61F 2013/00582; A61F 13/00; A61F 13/02; A61F 13/00008; A61F 13/06; A61F 13/00021; A61F 13/0209; A61F 13/022; A61F 13/0243; A61F 13/0246; A61F 13/025; A61F 13/0253
USPC ............... 604/304, 307; 424/443, 445, 448; 128/888–894; 602/41–43, 47, 52, 54–55, 602/58, 904
See application file for complete search history.

(56) References Cited

U.S. PATENT DOCUMENTS

2017/0135862 A1    5/2017  Tuck et al.
2020/0383839 A1*  12/2020  Rodzewicz ........... A61F 13/069

FOREIGN PATENT DOCUMENTS

| EP | 3260098 A1 | | 12/2017 | |
|---|---|---|---|---|
| GB | 1049196 A | * | 11/1966 | ......... A61F 13/0203 |
| JP | 2014168573 A | * | 9/2014 | |
| WO | WO-1996/10972 A1 | | 4/1996 | |
| WO | WO-0132121 A2 | * | 5/2001 | ............ A44B 99/00 |
| WO | WO 2007/113597 A2 | | 10/2007 | |
| WO | WO-2014/058532 A1 | | 4/2014 | |
| WO | WO-2016/030047 A1 | | 6/2015 | |

OTHER PUBLICATIONS

International Search Report and Written Opinion were dated Mar. 6, 2019 by the International Searching Authority for International Application No. PCT/EP2018/084742, filed on Dec. 13, 2018 and published as WO 2019/115685 dated Jun. 20, 2019 (Applicant—Mölnlycke Health Care AB) (11 Pages).

International Search Report and Written Opinion were dated Mar. 1, 2019 by the International Searching Authority for International Application No. PCT/EP2018/084744, filed on Dec. 13, 2018 and published as WO/2019/115686 dated Jun. 20, 2019 (Applicant—Mölnlycke Health Care AB) (12 Pages).

* cited by examiner

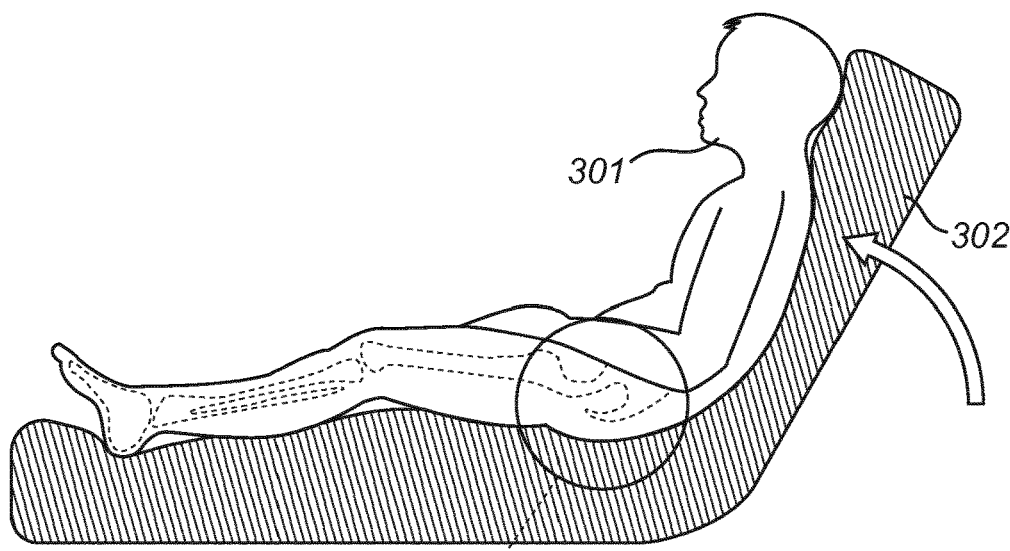
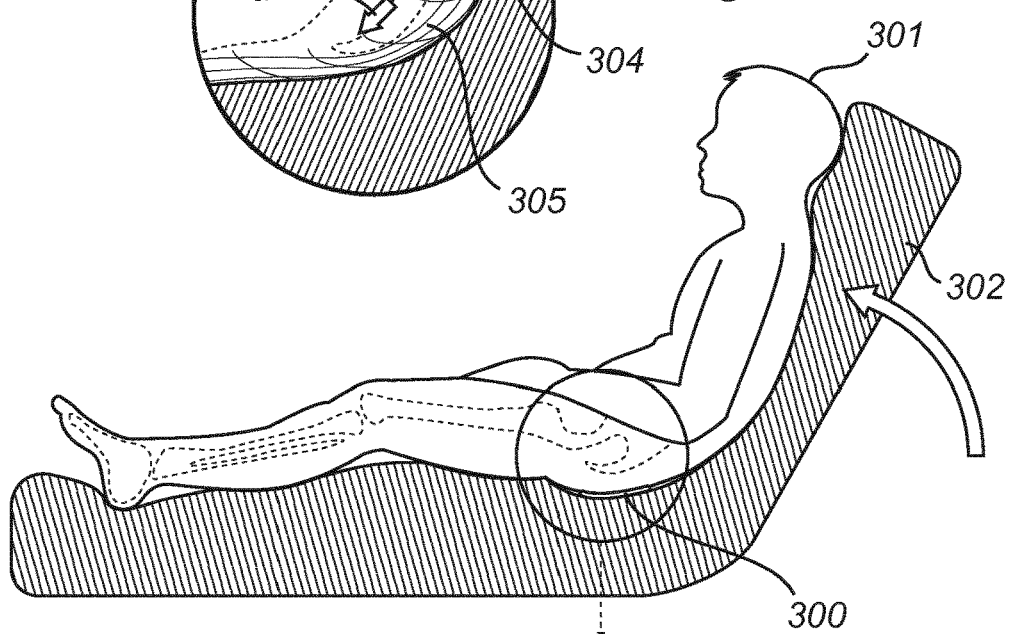
*Fig. 3a*
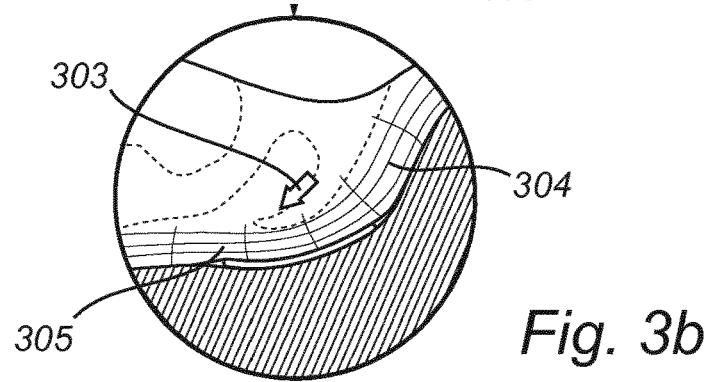
*Fig. 3b*

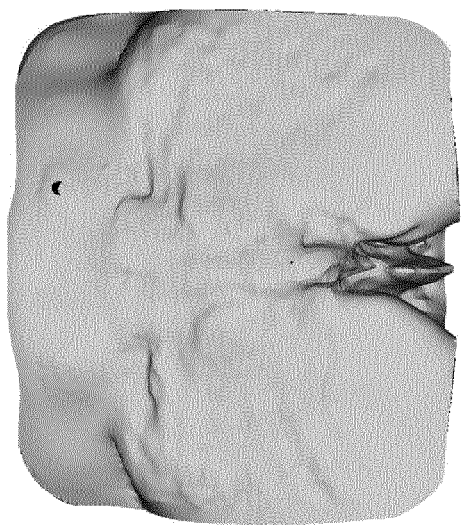
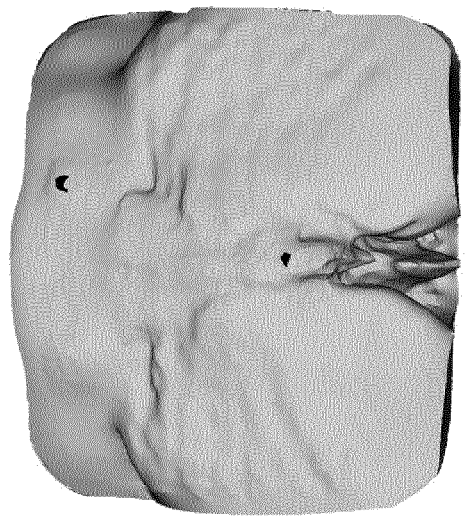
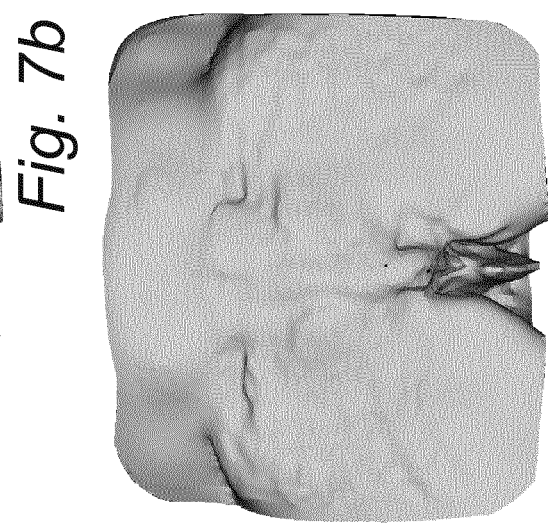
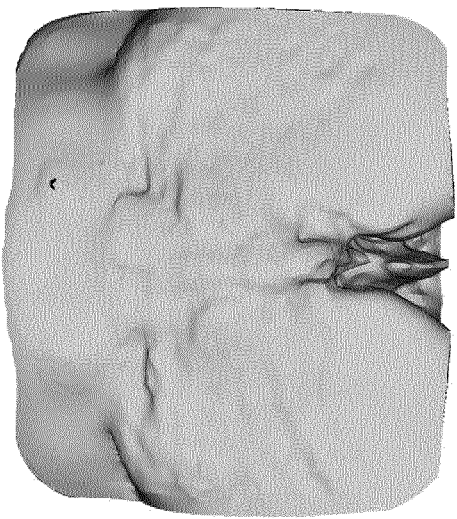

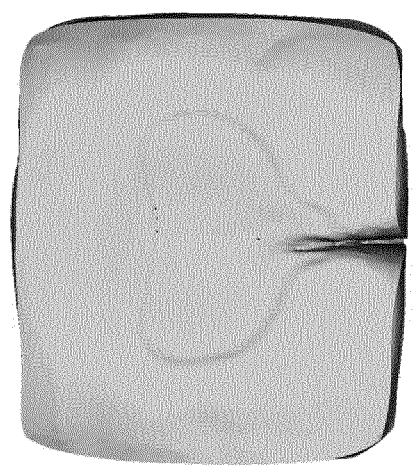
Fig. 9c
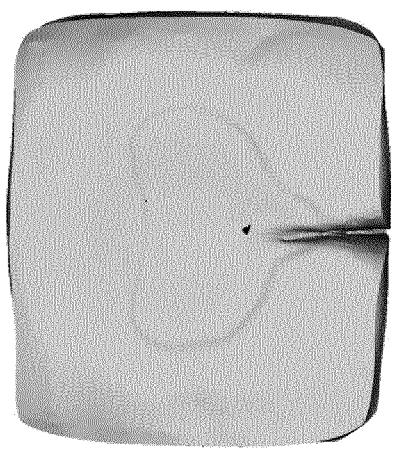
Fig. 9b
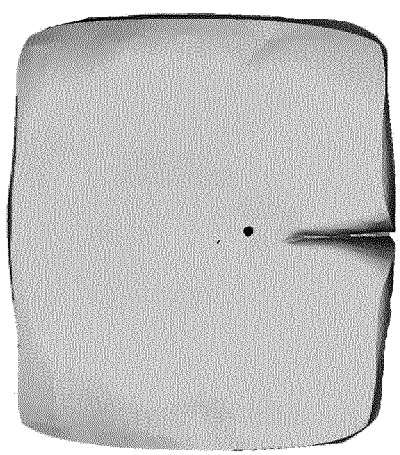
Fig. 9a

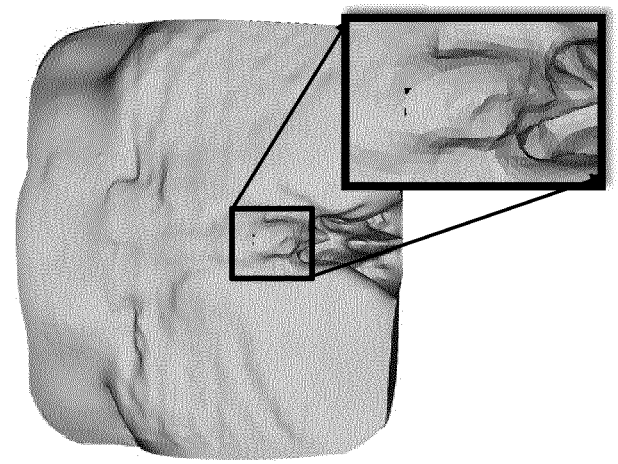
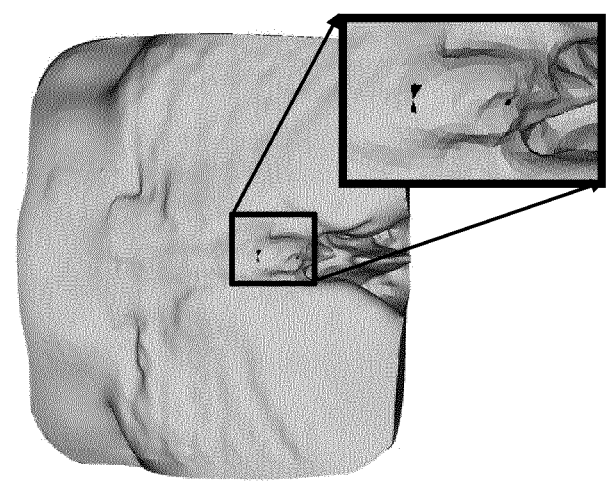
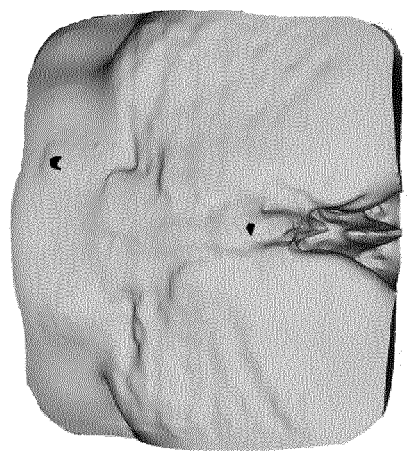
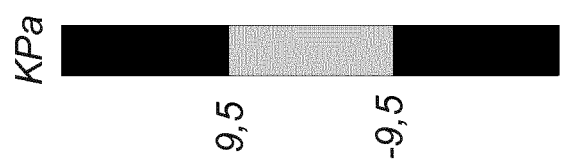
Fig. 10a  Fig. 10b  Fig. 10c

MEDICAL DRESSING

TECHNICAL FIELD

The present invention relates to a medical dressing comprising a backing layer a pad and an adhesive body contact layer. The dressing is suitable for prevention of pressure ulcers.

CROSS-REFERENCE TO RELATED APPLICATIONS

This application is a U.S. National Phase Application of International Application No. PCT/EP2018/084742, filed Dec. 13, 2018, which claims priority to European Application No. 17207754.7, filed Dec. 15, 2017, each of which are hereby incorporated by reference in their entirety.

BACKGROUND

A pressure ulcer is a localized injury to the skin and/or underlying tissue over a bony prominence that results from sustained pressure, often in combination with friction and shear. The major factors leading to pressure ulcers or pressure injuries are pressure, shear, friction and unfavourable microclimate. Other factors, intrinsic to patients, may also increase the likelihood of pressure ulcer development, e.g. poor perfusion, reduced sensation and inadequate nutrition. Pressure ulcers often arise among persons being bedridden for various reasons, such as for instance due to long term hospitalization or other causes of immobility. Pressure ulcers may also occur beneath medical devices, such as nasogastric tubes, ventilation masks and tracheostomy tubes, which are applied for diagnostic or therapeutic purposes. The rigid materials used in these devices may abrade the skin and create pressure on the soft tissues.

A pressure ulcer does not always start at the skin surface. What is observed at the skin is often only a small part of the sore, and this may mislead the patient or his/her caregiver to believe that there is only a minor problem.

Pressure ulcers often develop in soft tissue under the skin which covers bony areas of the body (so called "bony prominences"), for example the heels, ankles, the hips or the sacrum. Pressure and shear forces cause blood vessels to become squeezed between the skin surface and bone. Hence, muscles and tissue under the skin near the bone surface typically suffer the greatest damage. Accordingly, any pressure ulcer as apparent on the skin, regardless of how small, should be regarded as critical because of the probable damage below the skin surface.

A pressure ulcer can be classified into four categories: in the first category, the skin appears pink, reddened or discoloured, and may feel hard and warm to touch. In the second category, the skin breaks open and an ulcer that may look like a blister is formed. In this stage, the skin may be damaged beyond repair or may die. A category 3 pressure ulcer is an ulcer that extends into the tissue beneath the skin, forming a small crater. In category four, the pressure sore is very deep, reaching into the muscle and bone and causing extensive damage to deeper tissue and tendons. Serious complications, such as infection of the bone or blood can occur if the pressure ulcer progresses.

In a hospital or care facility, caregivers adhere to specific protocols to prevent the occurrence of pressure ulcers. One important part in the prevention regimen is regular inspection of the skin.

In some hospitals, caregivers apply wound dressings to areas at risk of developing pressure sores, for example in the sacrum, at the heels and under medical devices such as oxygen masks, and feeding, tracheostomy and nasogastric tubes. The dressings used are not primarily designed for prophylactic purposes.

Furthermore, when a dressing has been applied, the skin underneath the dressing must be regularly inspected, typically at least twice a day, to assess the skin status and ensure that there is no sign of damage. This requires the dressing to be peeled back to allow for assessment of the skin and any bony prominence covered. The dressing may need to be opened up and re-applied several times during the day. The adhesive capacity of dressing may thus be impaired.

Pressure ulcers are a global problem and the possibility to prevent these is desirable both to reduce human suffering but also to avoid unnecessary costs. The average cost for a category 3 or 4 pressure ulcer is from 75000 to 125000 US dollars per patient.

To summarize, there is a need to provide a dressing having an improved prophylactic effect; i.e. a dressing aimed at preventing a pressure ulcer from occurring in the first place and for preventing the progress of an already existing pressure ulcer. Furthermore, there is a need to provide for a proactive and cost-efficient means to relieve the burden for caregivers and staff dealing with pressure ulcers.

SUMMARY

In view of the above mentioned and other drawbacks of the prior art, it is an object of the present disclosure to provide improvements in relation to the prevention of pressure ulcers.

According to at least one aspect of the invention, there is provided a medical dressing for application to a surface of a human body; the dressing having a central portion and a surrounding border portion, wherein the dressing comprises a plurality of layers including:
  a backing layer,
  an adhesive body contact layer, and
  one or more pad-forming layers forming a pad arranged in the central portion between the backing layer and the body contact layer,
    wherein the backing layer and the body contact layer extend beyond the periphery of the pad to define the border portion along the contour of the pad;
    wherein the plurality of layers includes a first and a second anisotropic layer having anisotropic stiffness,
    wherein the medical dressing has a first direction (x) of extension and a second direction (y) of extension being perpendicular to the first direction (x) of extension, and
    wherein the stiffness of each one of the first and the second anisotropic layer is higher in the second direction (y) of extension than in the first direction (x) of extension.

As used herein, the term "stiffer" means that the anisotropic layer has a higher tensile force at 15% strain, as measured according to the tensile test described hereinafter.

As used herein, the term "anisotropic layer" means a layer that has anisotropic stiffness properties; i.e. the stiffness or stretchability is different in the first direction (x) of extension and the second direction (y) of extension of the layer. In the present invention, the "anisotropic layer" is stiffer in second direction (y) and more stretchable in the first direction (x).

The medical dressing is particularly useful for pressure ulcer prevention and/or pressure ulcer mitigation. The inventors have found that the incorporation of a layer having anisotropic stiffness properties into the dressing; i.e. an anisotropic layer being stiffer in a second direction (y) of extension than in a first direction (x) of extension has a preventative effect on the formation of pressure ulcers. Furthermore, by directionally aligning the stiffness of two different layers of the dressing, this effect may be enhanced. The directional stiffness is suitable for protecting the skin cells, and deeper tissue layer cells from harmful shear and compression forces resulting from exposure to pressure and/or sustained load, thereby preventing the onset of (or at least reducing the risk of) pressure ulcers.

In use, the dressing should be applied such that its second direction (y) corresponds to the direction of which the patient is exposed to most shear forces. For example, when the dressing is applied to the sacral region of a patient, the dressing is stiffer in the direction in which the patient slides in bed. This is normally along the length of the patient and therefore, in this application the second direction (y) of extension may, for convenience also be referred to as the longitudinal (y) direction. On the other hand, the first direction (x) of extension of the dressing is preferably more stretchable and pliable. This is beneficial since the first direction (x) of extension of the dressing normally corresponds to the direction by which the patient, wearing such dressing, will be turned and re-positioned by nursing personnel. Therefore, for convenience, in this application the first direction (x) of extension may also be referred to as the lateral (x) direction. However, it should be noted that, as used in this application, the terms longitudinal (y) and/or lateral (x) directions of the dressing, does not necessarily imply that the dressing is longer in one direction than in the other. For instance, the dressing may be substantially square shaped.

A bedridden patient at risk of developing pressure ulcers must be turned and repositioned at regular intervals. It is therefore important that the dressing conforms to this lateral movement and stays on the skin. Furthermore, the stretchability in the lateral (x) direction is advantageous since it prevents the skin and underlying tissues from becoming "over constrained" which could be the case if the dressing is too stiff in both the lateral and longitudinal directions.

A preventive effect has been found particularly advantageous in cases where one of the anisotropic layers is arranged in close proximity to the skin of a patient. This is reflected in at least some example embodiments, according to which at least the first anisotropic layer is the body contact layer or a sub-layer forming part of the body contact layer.

In at least some example embodiments, both the first anisotropic layer and the second anisotropic layer are sub-layers of the body contact layer.

The body contact layer may be provided with a plurality of apertures that provide or enhance the anisotropic characteristics of the body contact layer; and hence also the dressing. The apertures may suitably extend through the entire body contact layer in order to, additionally, serve to improve the absorption of fluid into the pad. The apertures may, for instance, be in the form of elongated cuts or elongated openings.

Thus, according to at least one example embodiment, the anisotropy of the body contact layer is provided by a plurality of elongated cuts or elongated openings, such as elliptical holes, in the body contact layer, wherein each elongated cut or elongated opening has a length direction and a width direction, and suitably, the length direction is the same as or parallel with the second direction (y) of extension, and wherein the width direction is the same as or parallel with the first direction (x) of extension.

This arrangement of apertures increases the stretchability in the first direction (x) of extension, but not substantially in the second direction (y) of extension. When the dressing and the patient are subject to stretching, e.g. due to turning of a patient, the elongated cuts or openings can extend in their width direction, which correspond to the first direction (x) of extension of the dressing.

According to at least one example embodiment the elongated cuts or elongated openings are provided in a plurality of rows extending in the second direction (y) of extension, wherein in each row the elongated cuts or elongated openings are aligned so that they all have the same length direction, wherein the plurality of rows includes a first set of rows and a second set of rows, wherein the elongated cuts or elongated openings of the first set of rows are offset in the second direction (y) of extension relative to the elongated cuts or elongated openings of the second set of rows.

Suitably, the first and the second set of rows may be arranged in such way that, in the first direction (x) of extension, rows of the first set of rows and rows of the second set of rows are provided alternatingly.

This arrangement of offset rows of elongated cuts or elongated openings results in an evenly distributed contact surface to the skin. In case of the body contact layer including an adhesive surface, its adhesiveness will accordingly be evenly distributed. Furthermore, the strength of the body contact layer become higher than if all the elongated cuts or openings of the different rows would be aligned, as such an alignment would risk functioning as an indication of fraction when loaded in the first direction (x) of extension.

According to at least one example embodiment, in each row the separating distance between two neighbouring elongated cuts or elongated openings, as measured centre-to-centre, is 1.5-16 mm. The number of holes per unit length may be varied dependent on the desired functionality. More holes per unit length allows for improved moisture absorption into the pad, but reduced adhesion. In contrast, fewer holes per unit length allows for improved adhesion but reduced absorption.

According to at least one example embodiment, in the first direction (x) of extension, each row from the first set of rows and a neighbouring row of the second set of rows are separated from each other, as measured centre-to-centre, by a distance of 0.9-4 mm.

According to at least one example embodiment, in the first direction (x) of extension, each row from the first set of rows and a neighbouring row of the second set of rows are separated from each other, as measured centre-to-centre, by a distance substantially corresponding to at least the width of the individual elongated openings, suitably at least twice the width of the individual elongated openings.

Again, the different separating distances may be chosen so that a desired balance is obtained between the absorption and adhesion abilities of the medical dressing, and such that the desired anisotropic properties of the body contact layer can be achieved.

According to at least one example embodiment, for each elongated opening the length direction extends from one curved end of the elongated opening towards an opposite curved end of the elongated opening. Although apertures in the form of elongated cuts or thin slits are within the scope of the inventive idea, and being included in at least some embodiments of the invention, the absorption capability of the medical dressing is improved if elongated openings, such as elliptical openings are provided as apertures in the body contact layer. Furthermore, by providing the elongated openings with curved ends the risk of the elongated openings causing an indication of fracture when the medical dressing is stretched, is reduced compared to if the apertures are in the form of slits. In some embodiments, each aperture may be a combination of slits and an elongated opening. For instance, each aperture may be formed as an elliptical opening, both curved ends thereof being directly adjacent to a respective slit (without any material portion present between the elongated opening and the slits).

According to at least one example embodiment each elongated opening has a length l and a width w, wherein $1.5w \leq l \leq 10w$, suitably $1.5w \leq l \leq 6w$. The length l and width w may be based, for instance, on the desired absorption capability and/or adhesiveness of the medical dressing. For instance, in at least some example embodiments the width w may be in the interval 0.5 mm-3 mm. In at least some example embodiments the length l may be in the interval 0.75-15 mm.

Furthermore, it has been found that the radius of curvature of the ends of the elongated openings are advantageously designed to be within a certain interval. According to at least some example embodiments, the radius of the curved ends of the elongated openings are in the interval w/12-w/2, i.e. the radius is no less than a twelfth of the width w, and not larger than half the width w. By providing the elongated openings with curved ends, such as with the above exemplified radius of curvature, sharp corners are avoided in the elongated openings and the risk of the elongated openings causing an indication of fracture when the medical dressing is stretched is reduced.

According to at least some example embodiments the apertures, whether in the form of elongated openings (such as elliptical openings) or elongated cuts/slits, may suitably cover 10-40% of the area of the body contact layer.

Accordingly, the adhesive surface represents 60 to 90% and is distributed evenly over the surface of the body contact layer. The dressing is thus kept in place during use. Furthermore, a greater coverage of adhesive on the skin facing surface aids in preventing undesirable friction forces which could form between the skin and the dressing as a patient slides in bed.

In at least some example embodiments, the smallest space between elongated openings is at least 0.75 mm. That smallest space, may for instance, be measurable obliquely to the first direction (x) and second direction (y) of extension, such as in the case of the openings forming a pattern of alternatingly mutually offset rows. This is advantageous, since a too small distance would potentially result in a thin material surface between the elongated openings which might easily break, especially if a person having the dressing applied is moving around in bed. Furthermore, the risk of lowered skin adhesion is also reduced with the above exemplified smallest space. In some embodiments the apertures, such as the elongated openings, of every second row may be offset half the distance between two apertures in a row.

As has been explained above, the first and the second anisotropic layer, may be respective sub-layers of the body contact layer. In other embodiments of the invention the first and the second anisotropic layer may be pad-forming layers.

In exemplary embodiments of the invention, the second anisotropic layer is one of the one or more pad-forming layers. It may be advantageous to distribute the effect of anisotropy over the thickness of the medical dressing. Thus, according to at least one example embodiment, the second anisotropic layer is one of the one or more pad-forming layers, and suitably the first anisotropic layer is the body contact layer (or a sub-layer thereof).

In alternative embodiments, the second anisotropic layer is integrated into the body contact layer. For example, the body contact layer may comprise an adhesive skin contact layer and the second anisotropic layer. If the adhesive skin contact layer is provided with a plurality of elongated cuts or elongated openings, this layer may serve as the first anisotropic layer, and the body contact layer thus comprises two anisotropic layers.

In embodiments, the body contact layer comprises three different layers; i.e. a plastic film, an adhesive skin contact layer and an anisotropic layer. The plastic film may be arranged between the adhesive skin contact layer and the anisotropic layer. Alternatively, the anisotropic layer is arranged between the skin contact layer and the plastic film. Besides improving the prophylactic effect by enhancing the anisotropy near the skin, this layered structure may also facilitate skin inspection. The integrity and rigidity of the body contact layer, and hence also the border portion, is increased. A caregiver must regularly inspect the skin beneath the dressing, which requires the dressing to be detached and re-attached several times a day. If the border portion is too thin and "flimsy", wrinkles may form when the dressing is re-applied to the skin. This may reduce the adhesive capacity of the border (and the body contact layer), and hence also the wear time of the dressing.

In at least some example embodiments, the second anisotropic layer has a tensile force at 15% strain in the second direction (y) of extension of at least 4 N, preferably at least 10 N, most preferably at least 15 N, as measured by the tensile test described herein.

The prophylactic effect of the dressing is thereby improved, and the skin cells and underlying soft tissue cells are protected from becoming extensively damaged. The structural integrity of the dressing is enhanced, and the pressure and shear forces inflicted on a patient laying down on a hospital bed (e.g. a bedridden patient) are reduced. Stiffness in the direction of shear exposure protects the skin cells and deeper tissue layer cells from stretching, and thereby deforming.

According to at least some example embodiments, the second anisotropic layer has a tensile force at 15% strain in the second direction (y) of extension that is at least 6 times higher, preferably at least 10 times higher than in the first direction (x) of extension, as measured by the tensile test described herein.

Accordingly, the stay-on ability of the dressing on the skin is enhanced, and the skin and underlying tissue is prevented from becoming over constrained which could otherwise be the case if the dressing is too stiff in both the first (x) and the second (y) directions.

The second anisotropic layer may comprise a nonwoven material, which may in addition to providing the anisotropic characteristics, also serve as a liquid acquisition layer.

In accordance with at least one example embodiment of the invention, the second anisotropic layer is an oriented fibrous nonwoven layer having more than 50% of the fibres oriented in the second direction (y). In this manner, the fibres oriented in the second direction (y) will provide reinforcement in this direction.

In exemplary embodiments, the dressing comprises at least one gripping tab; the gripping tab being coplanar with and projecting outwardly from the border portion of the dressing.

As mentioned, regular inspection of the skin is an important procedure in the hospital and caregiver routines for preventing pressure ulcers. The gripping tab facilitates inspection of the skin by guiding the caregiver to lift the dressing, inspect the skin underneath the dressing, and to thereafter re-apply the dressing onto the skin.

In another aspect, the invention relates to a dressing as described hereinbefore for use in the prevention of pressure ulcers.

However, although the primary use of the invention is for prevention, such a dressing may also be used in the treatment of pressure ulcers or wounds.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

FIGS. 3a and 3b illustrate a bedridden patient exposed to pressure and shear forces when the head of the bed is tilted upwards when no dressing is used (FIG. 3a), and when a dressing of the invention has been applied to the sacrum region of the patient (FIG. 3b).

FIG. 7 illustrates the Von Mises stress distribution at the muscle arising from compression in a Finite element (FE) model simulation, when no dressing is used (FIG. 7a), a foam pad (FIG. 7b), a dressing comprising anisotropic layer(s) in the body contact layer (7c), and a dressing comprising anisotropic layer(s) in the pad (FIG. 7d).

FIG. 9 illustrates the mean pressure (hydrostatic stress) distribution at the skin arising from compression in a Finite element (FE) model simulation, when no dressing is used (FIG. 9a), a dressing comprising anisotropic layer(s) in the pad (FIG. 9b) and a dressing comprising anisotropic layer(s) in the body contact layer (FIG. 9c).

FIG. 10 illustrates the Von Mises stress distribution at the muscle arising from compression in a Finite element (FE) model simulation, when no dressing is used (FIG. 10a), a dressing comprising anisotropic layer(s) in the pad (FIG. 10b) and a dressing comprising anisotropic layer(s) in close proximity of the skin (FIG. 10c).

DETAILED DESCRIPTION

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person.

Figure 1A:
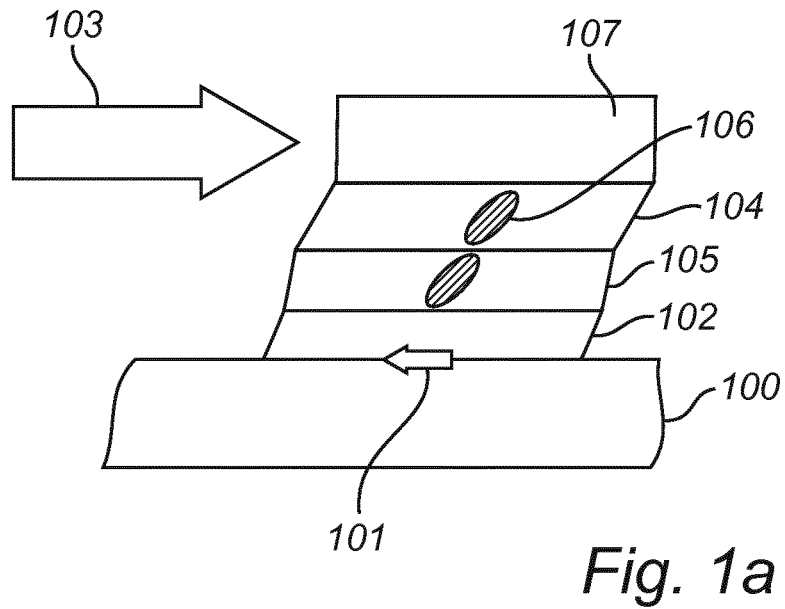
FIGS. 1a and 1b schematically illustrate how pressure, shear and friction contribute to the development of pressure ulcers.
Figure 1B:
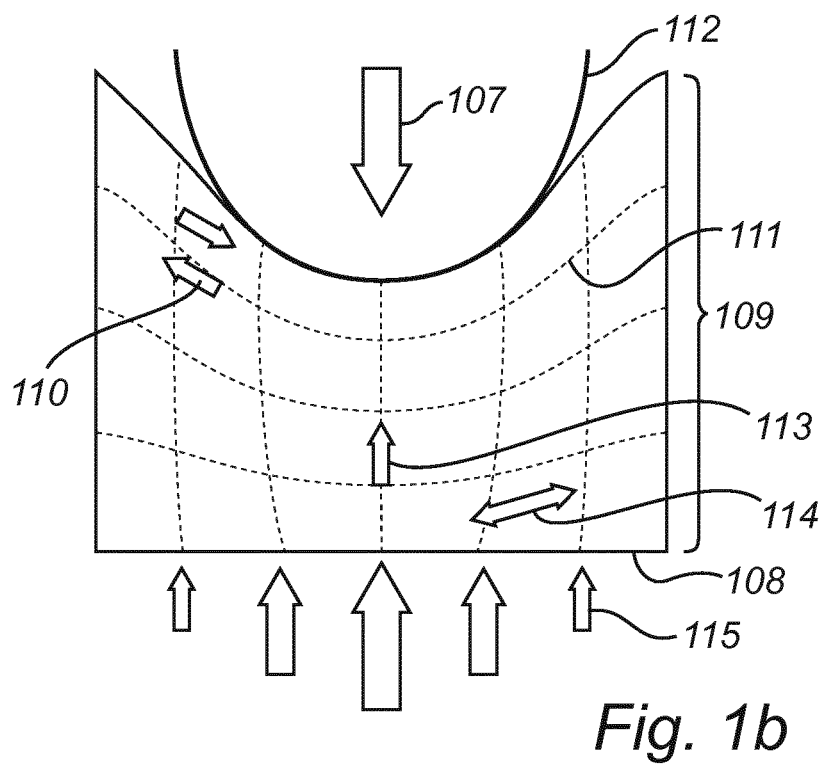

FIGS. 1a and 1b conceptually illustrate how pressure, shear and friction contribute to pressure ulcer development.

Referring to FIG. 1a, when a patient in contact with a support surface 100 moves, friction 101 between the skin 102 and the support surface 100 tends to hold the skin 102 in place and a shear force 103 occurs that displaces and deforms the deeper tissues (muscle 104 and adipose tissue 105). The deeper tissue layers 104 and 105 are subject to the worst effect of shear since these layers, in closer proximity to the bone 107, cannot move in a manner like the skin layer 102 does. Instead these layer are stretched but still "stuck". Furthermore, blood vessels 106 are distorted and compressed. Compression of blood vessels 106 by pressure and/or shear may reduce the blood flow to tissues. This may result in tissue hypoxia, build-up of metabolic waste products and, eventually, tissue damage.

Referring to FIG. 1b, when a force 107 is applied perpendicular to the surface of the skin, pressure is exerted onto the skin 108 and subcutaneous tissues 109. Pressure 107 compresses the tissues 109 and may distort or deform the skin and the soft tissues (e.g. subcutaneous fat and muscle). Shear 110 may also occur in and between layers 111 of deeper tissues as a result of tissue deformation caused by pressure over a bony prominence 112. Muscle is particularly prone to damage by shear. Compression stresses 113 occur in the axis perpendicular to the direction of the muscle fibers, and tensile stresses 114 occur when the tissue is stretched and deformed along the fiber direction. The arrows 115 represent surface pressure. Deformation of soft tissues is greater when pressure is applied over a bony prominence 112. Damage thus often occur initially in the soft tissue, i.e. at the muscle/bone interface, and skin breakdown and pressure sore formation occurs later in the process. Hence, when assessing a pressure sore, the full extent of the damage may not be clear or visible.

Figure 2A:
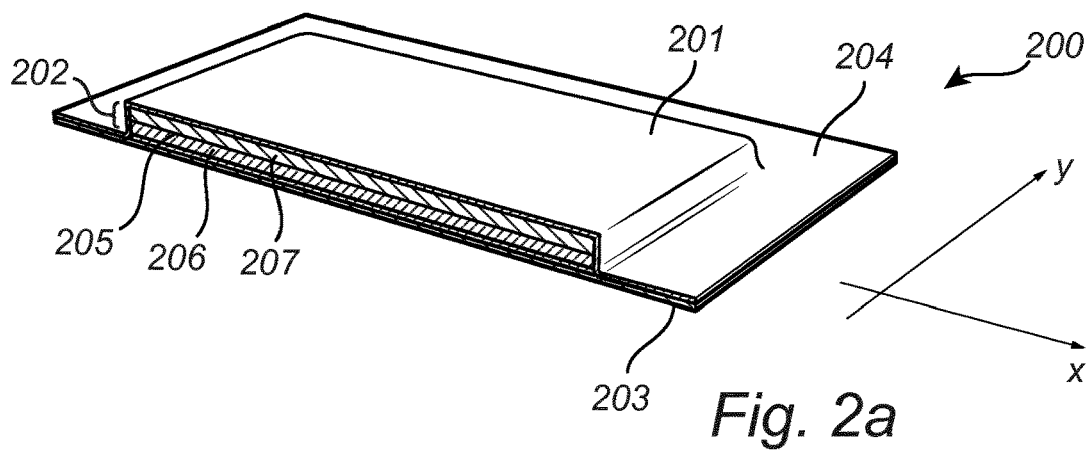
FIG. 2a is a cross-sectional view according to one exemplary embodiment of the present invention.

FIG. 2a illustrates a dressing according to an exemplary embodiment of the present invention. The medical dressing 200 has a first direction (x) of extension and a second direction (y) of extension. As previously explained, for convenience, in this application the first direction (x) of extension may also be referred to as the lateral (x) direction, while the second direction (y) of extension may, for convenience also be referred to as the longitudinal (y) direction. In this application, the terms longitudinal (y) and lateral (x) directions do not necessarily imply that the dressing is longer in one of the two directions (as illustrated in FIG. 2e, the dressing may have substantially equal extension in the longitudinal (y) and lateral (x) directions).

The dressing 200 comprises a backing layer 201, a pad 202, and a body contact layer 203, wherein the pad 202 is arranged between the backing layer 201 and the body contact layer 203 and wherein the backing layer 201 and the body contact layer 203 extend beyond the periphery of the pad 202 to define a border portion 204 around the contour of the pad. In this exemplary embodiment, the body contact layer is the first anisotropic layer and the second anisotropic layer 205 is arranged in the pad 202.

The pad 202 may comprise one or more pad-forming layers.

As illustrated in FIG. 2, the pad 202 comprises a second anisotropic layer 205 being stiffer in the longitudinal (y) direction than in the lateral (x) direction. The pad may be comprised of the second anisotropic layer 205 only, or may comprise one or more layers.

For example, the pad may comprise a material that yields a pressure-relieving effect, e.g. a foam or a gel. This layer is denoted 206 in FIG. 2b.

In embodiments the pad comprises a superabsorbent material e.g. superabsorbent polymers (SAP) or superabsorbent fibers (SAF).

In embodiments, the pad comprises a first superabsorbent layer 207, a second anisotropic layer 205 and a third pressure relieving layer 206, wherein the second anisotropic layer 205 is arranged between the first superabsorbent layer 207 and the third pressure relieving layer 206.

If the second anisotropic layer 205 is a nonwoven, it may also serve as a liquid acquisition layer.

This pad construction is beneficial from a microclimate point of view. Moisture absorbed into the dressing is quickly transported away from the layer closest to the skin (the third pressure relieving layer 206) to the first superabsorbent layer 207. Also, heat energy generated may be wicked away from the skin. Since heat increases the metabolism of the already stressed cells under pressure and shear, this could otherwise add to the deterioration of skin cells. The layered pad construction prevents accumulation of body liquids close to the skin.

In preferred embodiments, the body contact layer 203 comprises a plurality of apertures. The apertures improve the absorption of body fluids into the dressing without compromising the adhesiveness to the skin area. Furthermore, the apertures may have a shape that renders the body contact layer or a sub-layer of the body contact layer anisotropic.

In embodiments, the plurality of apertures is selected from a plurality of elongated cuts or elongated openings, such as elliptical holes, wherein each elongated cut or elongated opening has a length direction and a width direction, and wherein the length direction is the same as or parallel with the second direction (y).

This way, the anisotropic characteristics of the body contact layer are enhanced. When the skin is stretched, for example when a bedridden patient is turned, the elongated cuts or openings are stretched and extended in their width direction, which correspond to the lateral (x) direction of the dressing. However, the body contact layer still remains its stiffness in the longitudinal direction (y).

Figure 2B:
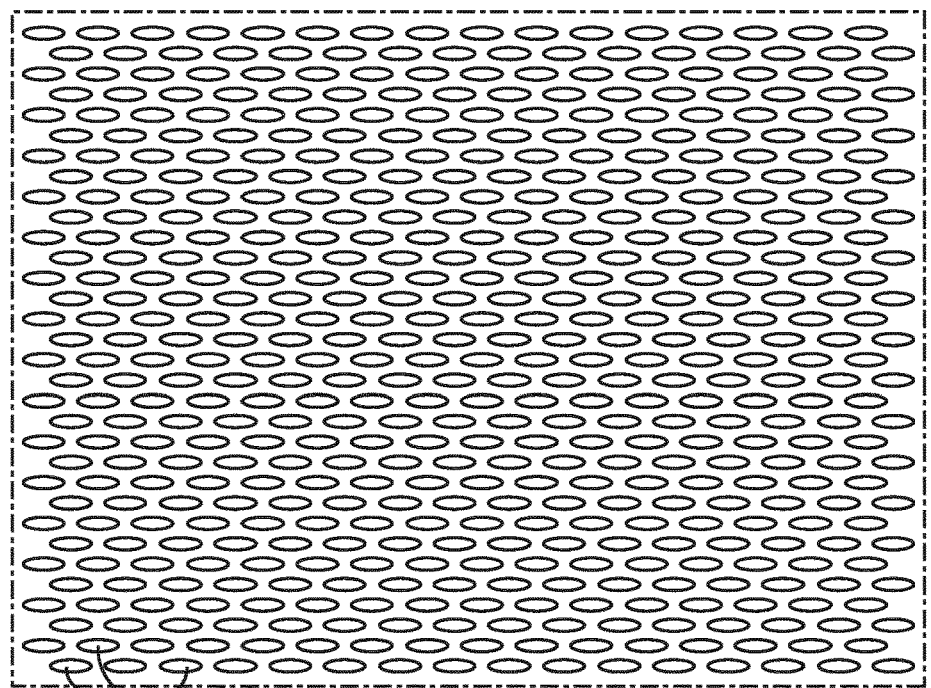
FIG. 2b illustrates an anisotropic body contact layer provided with elliptical apertures according to an exemplary embodiment of the invention.
Figure 2C:
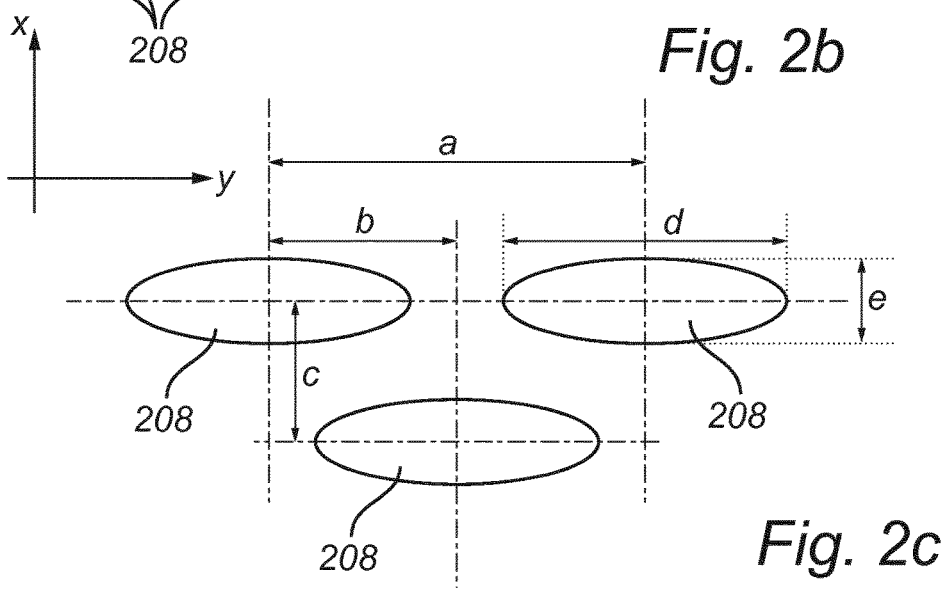
FIG. 2c is a zoomed in view of the body contact layer in FIG. 2b.

FIGS. 2b and 2c illustrate an example of how the apertures 208 in the body contact layer 203 may be distributed in the body contact layer 203 of FIG. 2a.

FIG. 2c illustrates a pattern of apertures 208 in the form of elongated openings, such as elliptical openings. The apertures 208 are arranged in parallel rows extending in the longitudinal (y) direction, which is also the length direction of each individual aperture 208 in a row. When viewing the pattern along the lateral (x) direction, every second row is longitudinally offset (suitably by half an aperture length). The apertures 208 may suitably cover 10-40% of the area of the body contact layer.

FIG. 2c schematically (not true to scale) illustrates exemplary dimensions of the apertures 208. The apertures may, for instance, have a length l and a width w, wherein $1.5w \leq l \leq 10w$, suitably $1.5w \leq l \leq 6w$. A suitable width w may be in the interval 0.5 mm-3 mm. The length l and width w may be based, for instance, on the desired absorption capability and/or adhesiveness of the medical dressing. In FIG. 2c, the width is denoted e, and the length is denoted d. The radius r of the curved ends of the apertures 208 may be in the interval w/12-w/2. The smallest space d between apertures may be at least 0.75 mm. As illustrated in FIG. 2c, that smallest space d is along a diagonal or oblique extension (relative to the longitudinal (y) and lateral (x) directions. In each row, the separating distance a between two neighbouring elongated cuts or elongated openings, as measured centre-to-centre may, for instance, be 1.5-16 mm, or (related to the length l of the apertures) for instance 1.1l-2l. The length l may, for instance, be 0.75-15 mm. Neighbouring rows may suitably be separated from each other, as measured centre-to-centre, by a distance c of, for instance, 0.9-4 mm, or (related to the width w of the apertures) for instance 1.3w-1.8w. The width w may, for instance, be 0.5-3 mm. Furthermore, the apertures of neighbouring rows may be offset relative to each other by a distance b of, for instance, a/2.

In some embodiments, the body contact layer comprises two anisotropic layers. In such exemplary embodiments, the anisotropic layer 205 in the pad may be omitted.

Figure 2D:
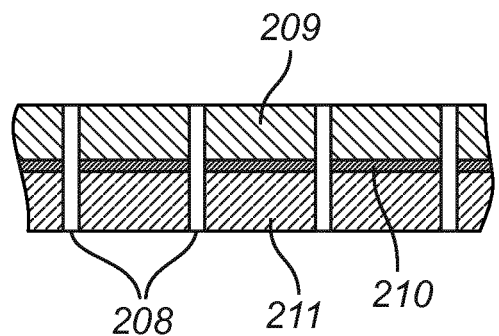
FIG. 2d illustrates a body contact layer according to an alternative embodiment of the present invention.
Figure 2E:
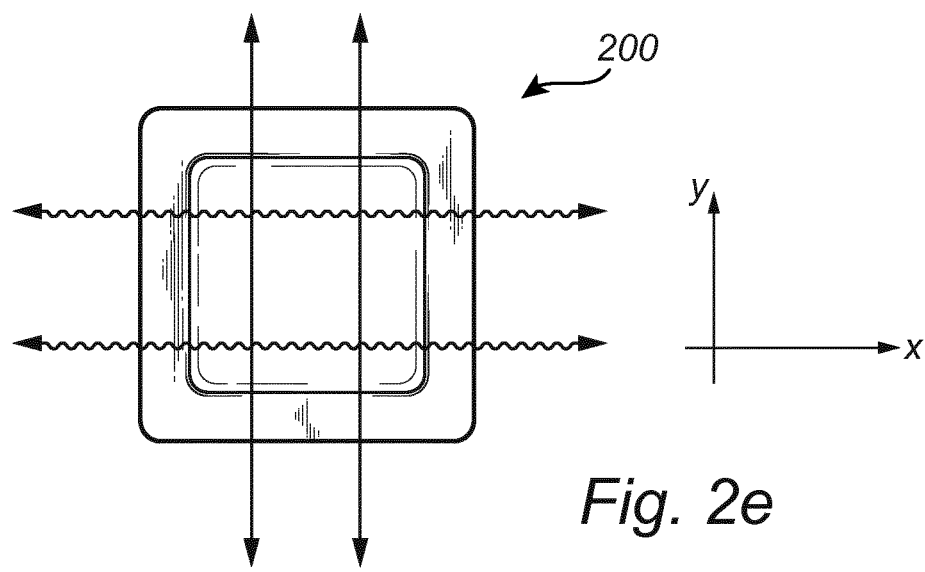
FIG. 2e illustrates the anisotropic properties of a dressing according to the present invention.

FIG. 2d illustrates a body contact layer according to an exemplary embodiment. In this embodiment, the body contact layer 203 comprises an anisotropic layer 209, a plastic film 210, and an adhesive skin contact layer 211.

As illustrated in FIG. 2d, the plastic film 210 is arranged between the anisotropic layer 209 and the adhesive skin contact layer 211. It is however equally conceivable that the anisotropic layer 209 is arranged between the plastic film 210 and the adhesive skin contact layer 211.

The body contact layer 203 comprises a plurality of apertures 208. The apertures 208 may extend at least through the adhesive skin facing layer 207. In the case where the body contact layer 203 comprises more than two layers or films, the apertures may extend through at least two of the layers of the body contact layer 203.

In embodiments, as illustrated in FIG. 2b, the apertures 208 extend through all the layers of the body contact layer 203.

In embodiments where the second anisotropic layer 209 is arranged in the body contact layer 203, the adhesive skin contact layer 211 (and preferably also the plastic film 210) have a shape that enhance the anisotropy, as described hereinbefore.

The anisotropic layer 209 affects the stiffness of the entire dressing. As illustrated by the arrows in FIG. 2e, the dressing 200 is stiffer in the second (y) direction and more stretchable in the first (x) direction.

Suitably, the anisotropic layers illustrated in FIGS. 2a and 2b (denoted 205, and 209, respectively) have a tensile force at 15% strain in the second (y) direction of at least 4 N, preferably at least 10 N, and most preferably at least 15 N, as measured by the tensile test described herein.

In exemplary embodiments, the tensile force at 15% strain in the second (y) direction is at least 6 times higher, preferably at least 10 times higher than in the first (x) direction, as measured by the tensile test described herein.

The advantages of providing directional stiffness in the second (y) direction will be described more fully with reference to FIG. 3 further on in the specification.

The anisotropic layer(s) 205 and/or 209 may be selected from a variety of materials such as nonwovens, films, textile materials, polymeric net materials as long as they exhibit the desired anisotropic stiffness properties. The anisotropic layer may comprise a plurality of reinforcement fibres or filaments extending in the longitudinal direction. The reinforcement fibres or filaments provide the layer with high tensile force in the longitudinal (y) direction. Films or nets made of e.g. polyethylene, polypropylene, polyester, polyurethane or silicone can be used as long as these materials have sufficient strength in the longitudinal direction (y) and sufficient anisotropic properties.

In embodiments, the anisotropic layer(s) 205 and/or 209 comprises a nonwoven. Suitable nonwovens for use as the anisotropic layer are meltblown, spunbond, spunlaced or carded nonwoven webs.

In exemplary embodiments, the anisotropic layer(s) 205 and/or 209 is an oriented fibrous nonwoven layer having more than 50% of the fibres oriented in the longitudinal (y) direction. In this manner, the fibres oriented in the longitudinal (y) direction will provide reinforcement in this direction.

Examples of suitable polymers for use in the nonwoven are polyethylene, polyesters, polypropylene and other polyolefin homopolymers and copolymers. For example, nonwoven webs comprising thermoplastic fibres of polypropylene and polyethylene fibres or mixtures thereof may be used. The webs may have a high content of thermoplastic fibres and contain at least 50%, e.g. at least 70% thermoplastic fibres. The nonwoven may be a mixture of polyethylene and viscose, e.g. in a 70:30 ratio. Natural fibres, for example cotton may also be used as long as they provide the desired properties. The basis weight of the nonwoven may be in the range of from 10 to 80 g/m2, e.g. of from 13 to 50 g/m2. The anisotropic layer may also be a spunbond-meltblown or spunbond-meltblown-spunbond (SMS) web.

The body contact layer may, as already discussed, comprise one or more sub-layers. Preferably, the body contact layer 203 comprises at least a plastic film 210 and an adhesive skin contact layer 211.

The plastic film 210 may be a breathable polyolefin based film comprising e.g. polyethylene, polyamide, polyester polyurethane or silicone. In exemplary embodiments, the plastic film 210 comprises polyurethane. Suitably, the plastic film 210 is a thin polyurethane film. For example, the film may be a polyurethane film having a thickness from 15 and 100 μm, e.g. from 20 to 80 μm, preferably from 20 to 60 μm.

In embodiments, the adhesive skin contact layer 211 comprises a silicone gel. The silicone gel is skin-friendly, and easy to remove without causing trauma. It is sufficiently adherent to skin such that the dressing stays in place, and maintains its adherence with repeated removal and re-application.

Examples of suitable silicone gels include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive layer is preferably at least 20 μm.

The body contact layer 203 may be a laminate. Lamination of the different layers in the body contact layer may be made in any suitable manner, such as by adhesive, stitching, extrusion coating, ultrasonic welding or thermowelding. Any commonly used type of adhesive may be used, such as curable adhesives, solvent based adhesives or thermoplastic adhesives.

The effect of a medical dressing exhibiting anisotropic stretching properties may be explained with reference to FIGS. 3a and 3b.

In FIG. 3b, a dressing 300 according to the present invention has been applied to the sacrum region of the patient 301 such that the stiff, second direction (y) corresponds to the direction of which the tissue is exposed to most shear and stretch (i.e. the sliding direction of a patient). When a dressing is applied to the sacrum region, the pressure forces are reduced by the dressing 300 and distributed over a larger area. This leads to pressure re-distribution and reduced magnitude of critical forces on the skin and underlying tissue. The shear forces 303 are reduced by the dressing 300 since the dressing is stiff in the direction in which the patient 301 slides in bed 302. Therefore, the stiff dressing 300 "locks" the skin and underlying tissues such that they do not stretch excessively in the region where the dressing 300 is applied. The fact that the dressing is flexible in the first direction (x) is advantageous since it prevents the tissues from becoming "over constrained". Instead, the sacral buttocks can spread gently and naturally.

The individual tissue cells 305 in the sacral region of the patient 301 are therefore maintained relatively intact. The stretching of the skin may still occur at skin areas outside the dressing (which areas are at less risk for pressure ulcer formation caused by deformation, pressure and shear). This way, pressure forces, shear forces and the stress and stretch on skin cells and the underlying tissue cells are minimized.

In exemplary embodiments, the dressing comprises at least one gripping tab; the gripping tab being coplanar with and projecting outwardly from the border portion of the dressing.

Figure 4:
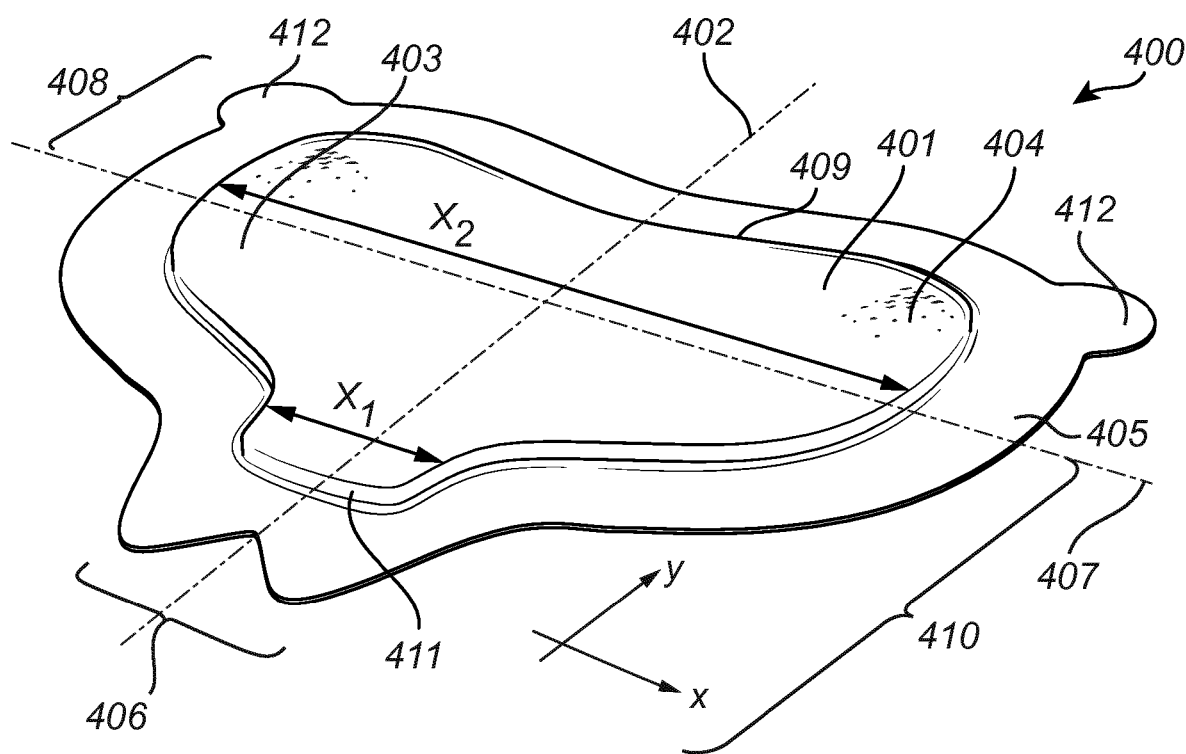
FIG. 4 illustrates an exemplary embodiment of a medical dressing according to at least another exemplary embodiment of the invention.

A dressing comprising two gripping tabs, and with a shape particularly suitable for application to the sacrum of a patient is illustrated in FIG. 4.

The medical dressing 400 illustrated in FIG. 4 has a lateral (x) extension and a longitudinal (y) extension; the pad 401 being symmetric about a longitudinal center line 402 and the dressing comprising a first lobed portion 403 on one side of the longitudinal center line 402 and a second lobed portion 404 on the other side of the longitudinal center line 402.

The first anisotropic layer of the body contact layer (and the second anisotropic layer of the pad, if present) is (are) arranged such that the first direction (x) of the first anisotropic layer corresponds to the lateral (x) extension of the dressing 400, and the second direction (y) of the anisotropic layer corresponds to the longitudinal extension of the dressing 400. Hence, the entire dressing is stiffer in the longitudinal (y) direction than in the lateral (x) direction.

The border portion 405 may be substantially heart shaped such that the first 403 and second 404 lobed portions form part of the lobed upper sides of a heart shape. Suitably, the first and second lobed portions are separated by a forked portion 406 which replaces the pointed lower part of a heart shape. The forked portion 406 comprises a protrusion on either side of an interstice located coaxially with the longitudinal center line.

The shape of the medical dressing 400 is adapted to fit to the sacral region of a human body. The forked portion 406 allows for an improved stay on ability in the gluteal cleft region. It is important that the dressing remains adhered in this region since otherwise body fluids (for example as a result of incontinence) may enter into the dressing and impair the adhesion to the skin.

The coccyx is an area exposed to a large amount of pressure and shear. It is therefore important to protect this part of the body, and the dressing suitably has a shape that allows for such protection.

Hence, the pad 401 may be divided by a lateral center line 407 into an upper pad region 408 having an upper lateral edge 409 and a lower pad region 410 having a lower lateral edge 411. The width, $x_1$, of the lower lateral edge 411 is between 10 and 40% of the maximum width, $x_2$, of the pad 401 in the lateral (x) direction.

The maximum width, $x_2$, of the pad of the dressing 400 is typically in the range of from 12 to 30 cm, e.g. from 15-20 cm. The width, $x_1$, of the lower lateral edge may be in the range of from 1 to 7 cm, e.g. from 2 to 4 cm, depending on the size of the dressing.

The gripping tab(s) 412 guides the caregiver to lift the dressing, inspect the skin underneath the dressing, and to thereafter re-apply the dressing onto the skin (in case the skin looks ok). Since the inspection of the skin typically takes place where the patient is lying on the side in the bed, it is beneficial to have at least two gripping tabs such that the caregiver can lift the dressing regardless of which side the patient lies. In FIG. 6, the gripping tab 412 is coplanar with and projects outwardly from the border portion of one of the lobed portions 403 and 404.

In exemplary embodiments, the friction coefficient of the backing layer is between 0.4 and 1 as measured by the standard test method ASTM D 1894-14.

The friction coefficient is preferably low such that the friction between the dressing and the bed sheet is reduced when a patient slides in bed. Reducing friction is an important aspect, since friction is the source of shear. The backing layer acts as a "sliding layer" and prevents the translation of friction into harmful shear forces.

The backing layer may be a thin film, sheet or membrane that is vapour permeable and waterproof. Examples of suitable materials for the backing layer include, but are not limited to polyurethane, polyethylene or polyamide films, silicone films, polyester based nonwoven materials, and laminates of polyester-based nonwoven materials and polyurethane films. Suitably, the backing layer is a polyurethane film having a thickness of from 5 to 40 μm, e.g. from 15 to 25 μm.

In embodiments, the backing layer comprises a functional enhancement print, wherein the functional enhancement print is asymmetric in the lateral (x) and longitudinal directions (y) in a non-stretched state.

The printed backing layer visually communicates to the user the differences in functionality of the dressing. It also aids in guiding the user to select a dressing suitable for prevention purposes, and to distinguish it from a dressing specifically directed towards treatment of wounds.

For example, the functional enhancement print may be a continuous print selected from a lattice of ellipses, rectangles and lines intersecting as crosses.

In another aspect, the invention relates to a dressing as described hereinbefore for use in the prevention of pressure ulcers.

However, although the primary use of the invention is for prevention, such a dressing may also be used in the treatment of pressure ulcers or wounds, especially low exuding wounds. A prophylactic dressing needs to be able to handle low exuding wounds and body fluids such as sweat, small amounts of blood, and pus.

Examples

Figure 5A:
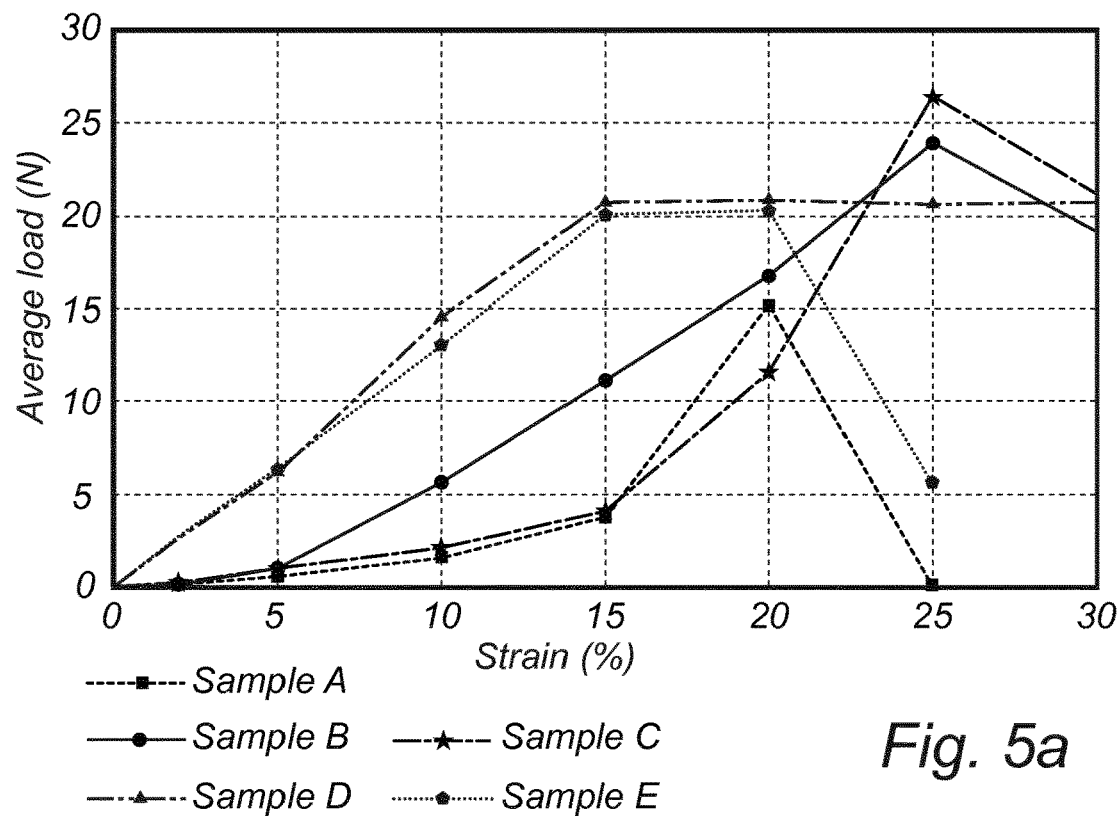
FIG. 5 illustrates the tensile curves for five different types of anisotropic layers in the second direction (y) (FIG. 5a) and in the first direction (x) (FIG. 5b).
Figure 5B:
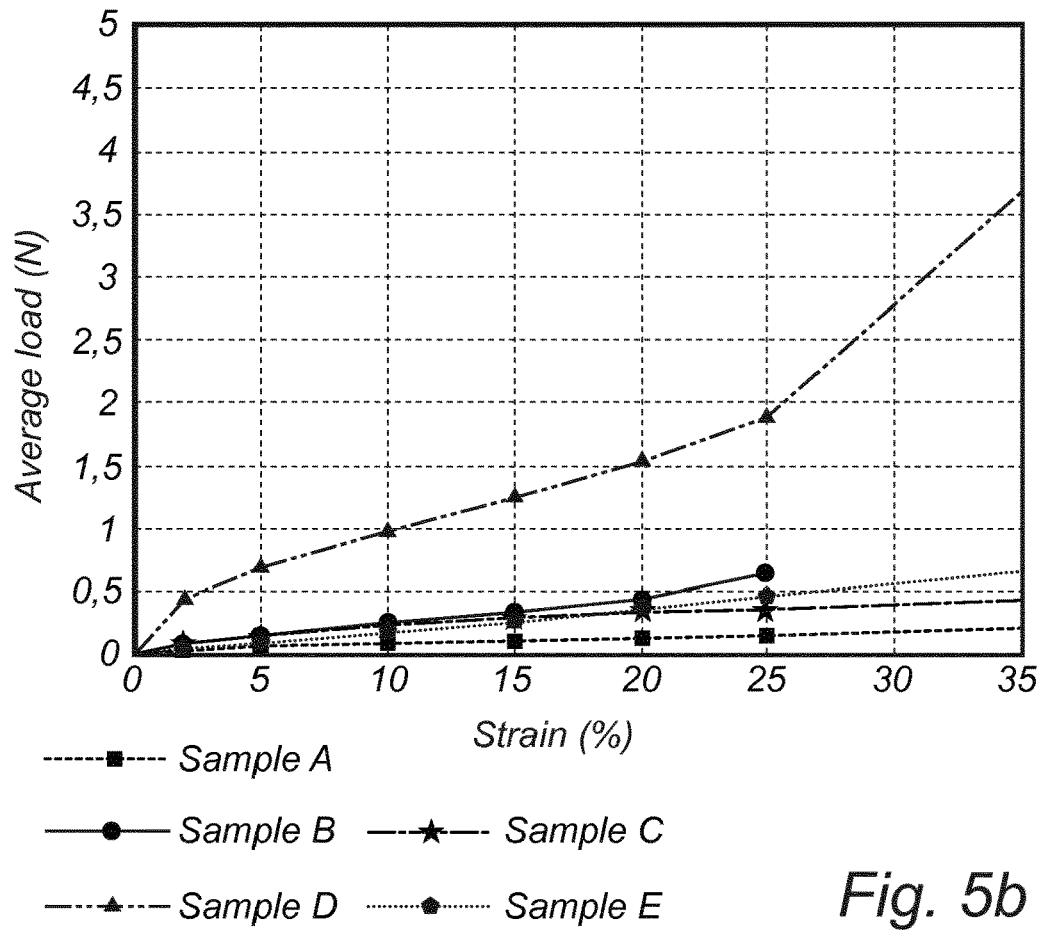

Tensile Force (Reference: ASTM D882-12)
    Apparatus: Tensile tester for e.g. MTS insight
    Tensile tester connected to a computer
    Crosshead speed: 50 mm/min
    Grip separation: 100 mm
    Sample preparation: Test specimens are punched from the material. The width of the specimens is 25 mm and the length at least 50 mm longer than the grip separation if possible. It is of importance that the edges of the specimens are even and without break notches. The specimens are conditioned for at least 24 h in 50 percent RH plus or minus 5 percent RH and 23 degrees centigrade plus or minus 2 degrees centigrade before testing.
    Procedure: The tensile tester is calibrated according to the apparatus instructions and set to zero. The sample is then mounted in the clamps and slack and pre-tension should be minimized. The tensile tester is started and the sample is elongated until break or until reaching 100% elongation, the tensile force (load) versus elongation is recorded. Measurements resulting from premature failures (i.e. the sample breaks at the clamp, or is damaged during preparation) are ignored if possible.
    The following results are expressed by the tensile tester/computer:
    Strain [%], extension/gage length
    Load at specific strain (e.g. at 15% strain)
    Five different anisotropic layers were tested, and their tensile curves are illustrated in FIG. 5. FIG. 5a illustrates the tensile curves in the second direction (y) and FIG. 5b illustrates the tensile curves in the first direction (x). Sample A was M33116-A (polyamide) from Eschler, sample B was M33116-B (polyamide) from Eschler, sample C was 322223 (polyester) from Eschler, sample D was 114160 Delstar (polyamide sample) from DEKA Medical, and sample E was a 40 gsm spunlace nonwoven comprising viscose and polyethylene (70:30).

Finite Element (FE) Modellinq

The mechanisms leading to pressure ulcers are not fully understood. Pressure sensing mats can give information on pressure present at the mattress under the skin surface but does not inform on the behaviour inside the soft tissues, at the origin of damage. Therefore, the Finite Element (FE) method offers a great alternative to study the biomechanisms of action for pressure ulcers.

The FE method is a numerical and computational technique used to solve multiphysics problems by solving partial differential equations upon different types of discretizations. The FE method subdivides a large problem or large 3D model into smaller parts called finite elements. The analyses are performed within each elements and the assembly gives a solution to the entire problem.

The workflow for a FE analysis can be explained as follows: creation of a 3D model constituted of finite elements, definition of the material properties of the model, definition of the boundary conditions and loadings to apply to the model according to the problem, computational solving of the problem, and analysis of the results through visualization and calculations.

FE Analysis to Investigate Anisotropy of Body Contact Layer

Body contact layers with different patterns of apertures and cuts were investigated to evaluate the creation of anisotropy. The tested body contact layers are illustrated in FIG. 6.

An isotropic body contact layer with a silicon adhesive and a carrier film was used as baseline for all designs. The body contact layer was constituted of materials isotropic in tension, and the material properties of the single carrier film and of the full body contact layer were post-processed from laboratory test data and validated. The thickness of the carrier film was 0.045 mm, and the total thickness of the body contact layer (silicone adhesive and carrier film) was 0.065 mm.

Figure 6A:
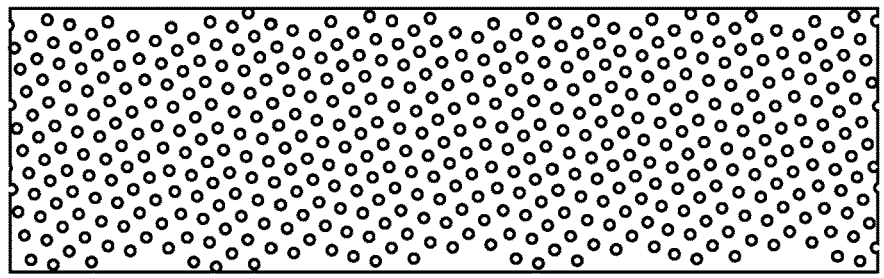
FIG. 6 illustrates five body contact layers having different patterns of apertures and cuts, according to prior art (FIGS. 6a and b) and according to the present invention (FIGS. 6c-e).

FIG. 6a illustrates a body contact layer with round apertures, wherein each aperture had a diameter of 1.4 mm and wherein the distance between neighbouring apertures was 1.4 mm.

Figure 6B:
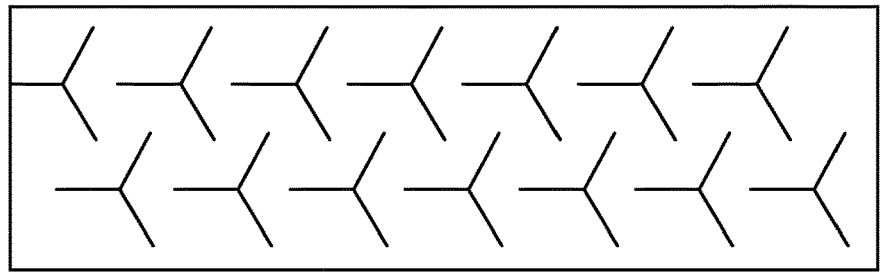

FIG. 6b illustrates a body contact layer comprising a pattern of incisions. Each "group of incisions" has a common starting point and three incisions extending therefrom. The length of each incision was 4 mm and, the width was 0.1 mm.

Figure 6C:
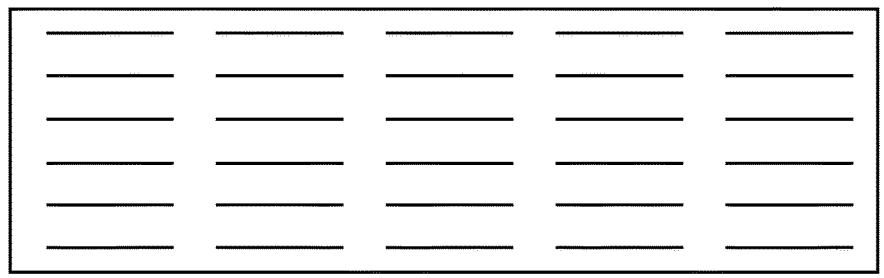

The body contact layer illustrated in FIG. 6c comprises columns of horizontal cuts. Each cut had a length of 15 mm, and the space between the cuts (both in the lateral (x) and longitudinal (y) directions) was 5 mm.

Figure 6D:
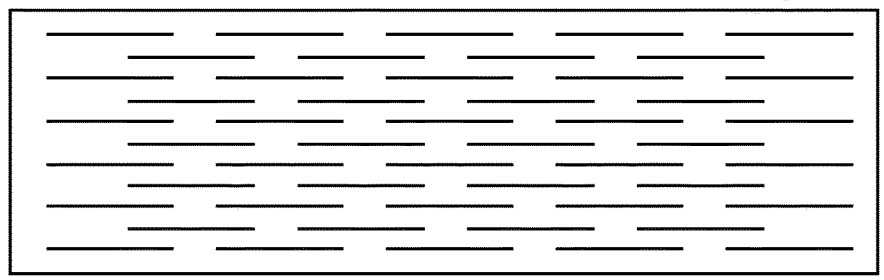

The body contact layer illustrated in FIG. 6d has a pattern of offset, alternating cuts, where the cuts has the same dimensions as those in FIG. 6c. The distance between one cut and another in the longitudinal (y) direction was 5 mm. The distance between one cut and another in the lateral (x) direction was 2.5 mm.

Figure 6E:
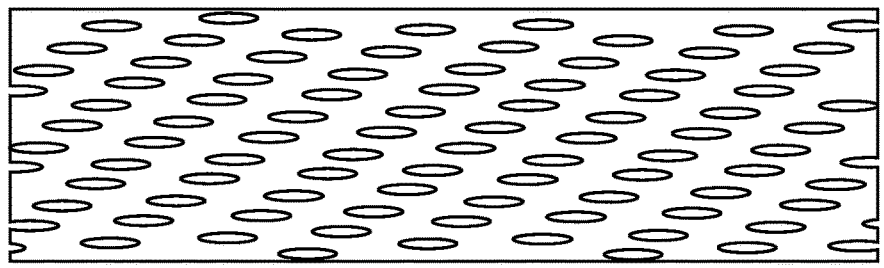

The body contact layer illustrated in FIG. 6e comprises a pattern of elliptical apertures. The length of each ellipse was 1.7 mm, and the width was 1.3 mm. The distance between the ellipses in the lateral (x) direction was 1.7 mm.

The test validation was performed by reproducing the laboratory tensile tests based on ASTM D882-12, where a rectangular sample is clamped at both extremities and elongated in one direction, with tensile tests simulated as:

The samples represented as rectangular shells, composed of triangular shaped elements (3-nodes elements), the rectangular shells having corresponding dimensions as in the laboratory test Sample width: 25 mm Sample length equivalent to grip separation of 200 mm The extremities of the samples were blocked (boundary conditions applied at the nodes), with displacement applied in the direction of the length of the sample Strains up to 20% original length were considered The output was the reaction forces (N) at one extremity and the equivalent displacements (mm)

The strain was calculated as the ratio of the displacement to the original length of the sample The anisotropic behavior of the body contact layers are presented in table 1 below.

TABLE 1

Tensile force at 15% strain for body contact layers with various shapes of cuts and apertures

| Sample | Tensile force at 15% strain in longitudinal (y) direction | Tensile force at 15% strain in lateral (x) direction |
| --- | --- | --- |
| Body contact layer according to FIG. 6a | 2.3 | 2.3 |
| Body contact layer according to FIG. 6b | 1 | 0.9 |
| Body contact layer according to FIG. 6c | 2.9 | 1 |
| Body contact layer according to FIG. 6d | 2.9 | 0.7 |
| Body contact layer according to FIG. 6e | 2.6 | 0.5 |

These results show that the design of the apertures can affect the anisotropy in the body contact layer.

Finite Element (FE) Settings and Anatomical Model for Studying the Impact of Anisotropic Dressings on the Skin and Deeper in the Soft Tissue In order to understand the effect of the dressing according to the present invention, finite Element (FE) models of a pelvis and of dressings according to the invention were created and analyses were performed to study the effect of pressure and stresses on the skin and in deep tissue layers. The volunteer was a non-smoker healthy adult male of 31 years at the time of the study (year birth 1984, length: 183 cm, weight: 77 kg).

The FE models were prepared in prepared in ANSA 16.0.1 and 17.1.0 (BETA CAE) and the analysis performed in ABAQUS 14.0 (DASSAULT SYSTEM). The FE model of the pelvis was segmented from MRI scans of the pelvis in order to insure the best anatomical accuracy.

The soft tissues were represented as non-linear materials (the muscles were lumped together as one material, the fat and the skin were lumped together as one compressive material), the bones as rigid body. The deformation of the soft tissue caused by compression from the body weight was used to validate the FE model and its material properties with ABAQUS 14.0 (DASSAULT SYSTEM). The validation was carried out by comparing the thickness of the soft tissues before and after compression between the model and the MRI data.

The deformation of the soft tissue was performed by simulating a clinical setting where a patient is lying on a mattress. A soft mattress (30 kPa) was added under the pelvis and the equivalent of the body weight was applied to induce contact and compression of the pelvis on the mattress. The deformation of the soft tissue due to pure compression was simulated with a vertical displacement of the body on the mattress.

The following soft tissue layers were investigated for stress distribution, and the following stresses were analysed:

TABLE 2

Soft tissue layers and simulated stresses

| Soft tissue layer | Definition of soft tissue layer | Stresses in compression |
| --- | --- | --- |
| At the skin | Posterior part of the skin/fat lump | Mean pressure |
| At the muscle | Posterior part of the muscle, interface between the muscle and the fat | Von Mises stresses, VMS |

"Stresses in compression" means the stresses that arise from compression; i.e. defined as the vertical displacement of the body on a mattress to mimic the compression of the pelvis when the patient is lying horizontally on a mattress.

The mean pressure (or hydrostatic stress) and the Von Mises stresses give an overview of the strain energy density and help to capture the origins of the strains and stresses in the tissues.

The Von Mises Stresses (VMS) are defined in the Distorsion Energy Theory and represent a common criterion widely used in engineering. The VMS can be defined as:

$$\sigma_{VM} = \sqrt{\frac{1}{2}[(\sigma_{xx} - \sigma_{yy})^2 + (\sigma_{yy} - \sigma_{zz})^2 + (\sigma_{zz} - \sigma_{xx})^2] + 3(\tau_{xy}^2 + \tau_{yz}^2 + \tau_{zx}^2)}$$

The Mean Pressure (or hydrostatic stress) can be defined as:

$$\sigma Hyd = \frac{1}{3}(\sigma xx + \sigma yy + \sigma zz)$$

The strain energy density is separated into different components in order to isolate the hydrostatic stresses and the deviatoric stresses. The deviatoric stresses are represented by the VMS and combine stresses in different directions into an equivalent stress that will take into account normal stresses, shear stresses and distortion. Combined with the hydrostatic stresses, the VMS can give an overview of the separate components of the strain energy density and help to capture the origins of the strains and stresses in the tissues.

The physical and mathematical relationship between force, stress, displacement and strain are the following:

Strain ε is defined as "deformation of a solid due to stress" and can be expressed as:

$$\varepsilon = dl/L_o$$

wherein
dl=change of length or displacement (mm)
$L_o$=initial length (mm)

The Young's modulus E (MPa) is a property of the material and can be defined as:

$$E = \sigma/\varepsilon$$

Shear stresses are stresses parallel to the plane and can be expressed as:

$$\tau = F_p/A$$

wherein
τ=shear stress (MPa)
$F_p$=parallel component force (N)
A=area (mm²)

There are no known values of critical stresses, as it varies between individuals, due to their physiological parameters, health, age and with the duration of exposure to the stresses. Therefore, the evaluation of the effect of the dressings relies on qualitative values. In the FIGS. 5-8, the black areas show higher stresses (critical values of stresses). Critical values of stresses have been defined as high value of stresses showing difference with "no dressing" and the dressings. The critical value of stresses correspond to about 1 kg for 10 cm2 (around 10 kPa).

Effect of Inventive Dressing

The following simulations were performed to study the prophylactic effect of the anisotropic dressing.
a) No dressing
b) Foam pad only
c) Dressing with foam pad and a simulated anisotropic body contact layer having a tensile force at 15% strain of 20.6 N in the second (y) direction, and of 0.3 N in the first (x) direction (referred to as Dressing A).
d) Dressing with foam pad and a simulated anisotropic pad-forming layer having a tensile force at 15% strain of 20.6 N in the second (y) direction, and of 0.3 N in the first (x) direction (referred to as Dressing B)

The dressings were created from technical CAD drawings and the simulated anisotropic layer(s) refers to a shell having a tensile force at 15% strain 20.6 N in the second (y) direction, and 0.3 N in the first (x) direction. In the simulations, the skin-facing surface of the dressings was fully adherent to the skin.

The shell simulated as the body contact layer may comprise one or several layers. In other words, Dressing A may represent the case when the anisotropy is provided by means of two anisotropic layers being incorporated into the body contact layer, e.g. by means of a first adhesive skin facing layer comprising elongated openings (wherein the length direction of the openings is parallel to the second direction (y) of extension) and when a second anisotropic layer is a sub-layer of the body contact layer. Furthermore, Dressing B may represent the case when the anisotropy is provided by means of two pad-forming layers.

The material properties of the different dressings were defined by actual laboratory measurements in tension and compression based on ASTM D 882-12 and ASTM D 3574-11.

Simulations were performed to analyze the stresses in compression (von Mises stresses) in the soft tissue layers muscle, and fat, respectively.

FIG. 7 illustrates the distribution of critical Von Mises stresses (black spots) at the muscles in the sacrum region after exposure to compression. FIG. 7a illustrates the critical von Mises stresses in the muscle when no dressing has been applied, FIG. 7b illustrates the critical Von Mises stresses when a dressing comprising a foam pad has been applied, and FIGS. 7c and 7d illustrate the critical von Mises stresses when the Dressing A, and B, respectively, have been applied.

As can be seen in FIG. 7, the volume of muscle under critical VMS stress was substantially reduced when a dressing comprising anisotropic layers was used (FIGS. 7c and 7d).

Another way to evaluate the performance of the dressings is to define its ability to reduce the volume of tissue under critical stresses. Critical values of stresses are defined as high value of stresses showing difference with "no dressing" and the dressings. As mentioned, for the Von Mises Stresses, the critical value of stresses correspond to about 1 kg for 10 cm2 (around 10 kPa).

The performance of the dressing can therefore be defined as the percentage reduction of volume of tissue under critical stress when compared to no dressing:

$$\text{Reduction } (\%) = \frac{(V_{nd} - V_d)}{V_{nd}} \times 100$$

with Reduction (%)=percentage reduction of volume of tissue under critical stress
with $V_{nd}$=Volume of tissue under critical stress with no dressing
with $V_d$=Volume of tissue under critical stress with dressing The percentage of reduction of the volume of soft tissue (muscles) subject to critical VMS stresses is summarized below.

TABLE 3

Percentage reduction of volume of muscle under critical VMS stress

|  | Foam pad | Dressing A | Dressing B |
|---|---|---|---|
| Reduction of volume of muscle under critical VMS stress | 56.4% | 79.8% | 85% |

As illustrated in table 3, the volume of muscle under critical VMS stress was substantially reduced when a dressing comprising anisotropic layers was used.

Figure 8:
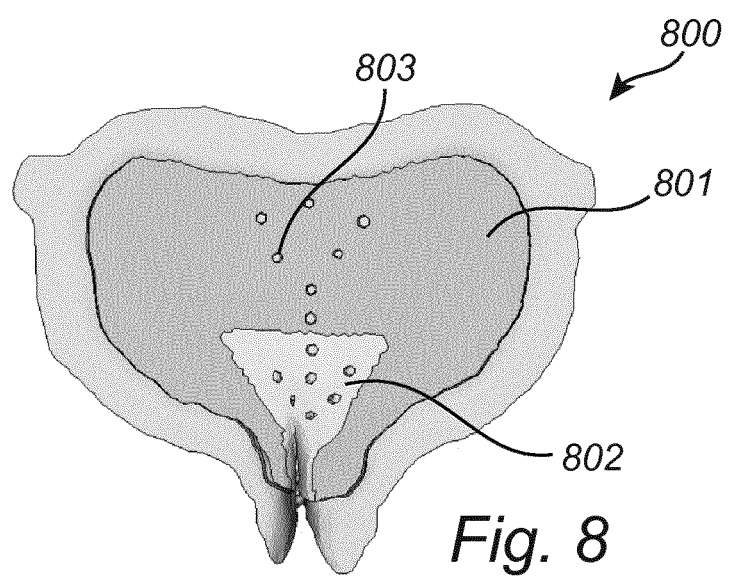
FIG. 8 illustrates a simulated gel based dressing with a central pad zone comprising apertures and a lower pad region with a lower gel compressive strength.t
Figure 11:
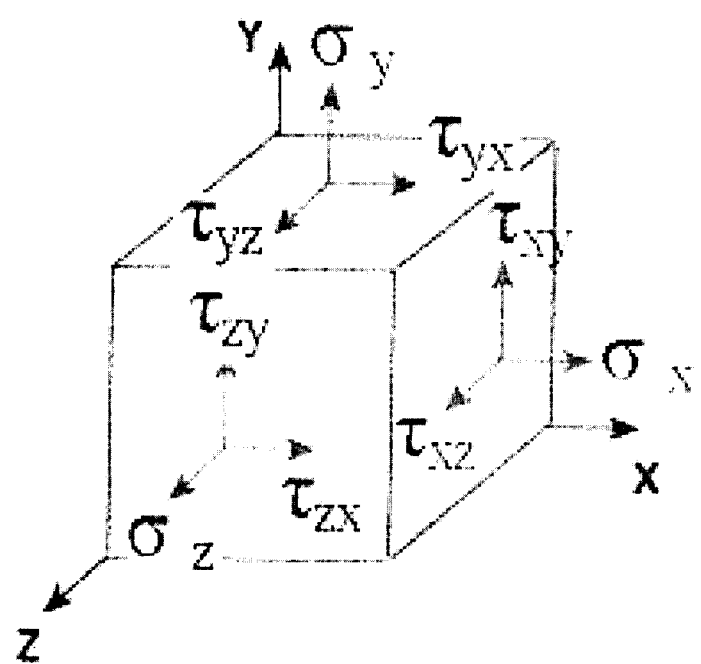
FIG. 11 is a schematic illustrating the orientation in space of the variables used to calculate the Von Mises stresses.

In the second set of simulations, two different types of gel based dressings were simulated. The general construction of the simulated dressings is illustrated in FIG. 8. The dressing 800 comprised a gel pad 801, wherein the gel had a Youngs modulus of 8 kPa, except for in the coccyx region 802 of the pad, where the Youngs modulus was 6 kPa. Apertures 803 were provided in the central zone of the dressings, and an intermediate, isotropic layer was inserted to the gel (to stabilize for the low compressibility of the gel). Both dressings comprised a simulated anisotropic shell having a tensile force at 15% strain of 20.6 N in the second (y) direction, and of 0.3 N in the first (x) direction. The difference between the two gel based dressings was the location of the anisotropic layers: in the middle of the dressing (referred to as Gel dressing A), and in the body contact layer; i.e. in close proximity of the skin (referred to as Gel dressing B).

FIG. 9 illustrates the critical hydrostatic stress (mean pressure) distribution at the skin in the sacrum region after exposure to pressure and compression for Gel dressing A (FIG. 9b), Gel dressing B (FIG. 9c) compared to when no dressing was used (FIG. 9a). As can be observed, the anisotropic layers reduce the critical compression stresses at the skin compared to when no dressing is used. Surprisingly, this effect is enhanced when the anisotropic layer is incorporated into the body contact layer; i.e. when the anisotropy is localized in close proximity of the skin (FIG. 9c).

The effect was also analyzed deeper in the soft tissue; i.e. at the muscle. FIG. 10 illustrates the distribution of critical VMS stresses at the muscle (shown as black spots) when no dressing has been used (FIG. 10a) compared to Gel Dressing A (FIG. 10b) and Gel dressing B (FIG. 10c). As can be seen, the anisotropic layers remarkably reduce the critical VMS stresses, and the protective effect on soft tissue is further enhanced when the anisotropic layer(s) is arranged close to the skin (in the body contact layer) as illustrated in FIG. 10c.

The effect of the dressing can also be represented as a calculation of the volume of soft tissue (muscle) subject to critical VMS stresses, as illustrated in table 4 below.

TABLE 4

Percentage reduction of volume of muscle under critical VMS stress with gel dressings A and B

|  | Gel dressing A compared to no dressing | Gel dressing B compared to no dressing |
|---|---|---|
| % reduction of volume of muscle under critical VMS stress | 88.2% | 99.2% |

Other embodiments of the invention will be apparent to those skilled in the art from consideration of the specification or practice of the invention disclosed herein. It is intended that the specification and examples be considered as exemplary only, with the true scope of the invention being indicated by the following claims.

The invention claimed is:

1. A medical dressing for application to a surface of a human body; the medical dressing having a central portion and a surrounding border portion, wherein the medical dressing comprises a plurality of layers including:
   a backing layer,
   an adhesive body contact layer, and
   one or more pad-forming layers forming a pad arranged in the central portion between the backing layer and the body contact layer,
   wherein the backing layer and the body contact layer extend beyond a periphery of the pad to define the border portion surrounding the pad;
wherein the plurality of layers includes at least a first and a second anisotropic layer having anisotropic stiffness,
   wherein the first anisotropic layer is:
      A) the body contact layer, or
      B) a sub-layer coextensive with the body contact layer and forming part of the body contact layer,
   wherein the medical dressing has a first direction (x) of extension and a second direction (y) of extension being perpendicular to the first direction (x) of extension, and
wherein a stiffness of each one of the first and the second anisotropic layers is higher in the second direction (y) of extension than in the first direction (x) of extension.

2. The medical dressing according to claim 1, wherein anisotropy of the body contact layer is provided by a plurality of elongated cuts or elongated openings in the body contact layer, wherein each of the plurality of elongated cuts or elongated openings has a length direction and a width direction.

3. The medical dressing according to claim 2, wherein the plurality of elongated cuts or elongated openings are provided in a plurality of rows extending in the second direction (y) of extension, wherein in each row of the plurality of elongated cuts or elongated openings are aligned so that they all have a length direction that is the same, wherein the plurality of rows includes a first set of rows and a second set of rows, wherein elongated cuts or elongated openings of the first set of rows are offset in the second direction (y) of extension relative to elongated cuts or elongated openings of the second set of rows.

4. The medical dressing according to claim 3, wherein, in the first direction (x) of extension, rows of the first set of rows and rows of the second set of rows are provided alternatingly.

5. The medical dressing according to claim 3, wherein, in the first direction (x) of extension, each row from the first set of rows and a neighbouring row of the second set of rows are separated from each other, as measured centre-to-centre, by a distance substantially corresponding to at least a width of individual elongated openings, suitably twice the width of the individual elongated openings.

6. The medical dressing according to claim 2, wherein the length direction is the same as or parallel with the second direction (y) of extension, and wherein the width direction is the same as or parallel with the first direction (x) of extension.

7. The medical dressing according to claim 2, wherein for each elongated opening the length direction extends from one curved end of the elongated opening towards an opposite curved end of the elongated opening.

8. The medical dressing according to claim 2, wherein each elongated opening has a length l and a width w, wherein 1.5w≤l≤10w.

9. The medical dressing according to claim 2, wherein the elongated cuts or elongated openings cover 10-40% of the area of the body contact layer.

10. The medical dressing according to claim 1, wherein the second anisotropic layer is one of the one or more pad-forming layers.

11. The medical dressing according to claim 10, wherein the second anisotropic layer has a tensile force at 15% strain in the second direction (y) of extension of at least 4 N, as measured according to ASTM D882-12.

12. The medical dressing according to claim 10, wherein the second anisotropic layer has a tensile force at 15% strain in the second direction (y) of extension that is at least 6 times higher than in the first direction (x) of extension, as measured according to ASTM D882-12.

13. The medical dressing according to claim 10, wherein the second anisotropic layer comprises a nonwoven material.

14. The medical dressing according to claim 1, wherein the second anisotropic layer is integrated into the body contact layer.

15. The medical dressing according to claim 1, wherein the body contact layer comprises a plastic film and a silicone adhesive, the silicone adhesive being arranged to contact the skin.

16. A method comprising:
a) applying the medical dressing according to claim 1 to a subject at an area of risk of developing a pressure ulcer, thereby reducing the risk of developing of a pressure ulcer at the area.

* * * * *